United States Patent
Brysch

[11] Patent Number: 5,823,773
[45] Date of Patent: Oct. 20, 1998

[54] DENTAL TRAY LINER AND METHOD

[76] Inventor: Wendy L. Brysch, Rte. 1, Box 189E, Hobson, Tex. 78117

[21] Appl. No.: 790,265

[22] Filed: Jan. 28, 1997

[51] Int. Cl.[6] .................................................. A61G 15/00
[52] U.S. Cl. ............................................. 433/77; 433/229
[58] Field of Search .............................. 433/77, 78, 229; 434/263

[56] References Cited

U.S. PATENT DOCUMENTS

| | | | |
|---|---|---|---|
| D. 202,618 | 10/1965 | Maurer et al. | 433/79 |
| 1,645,387 | 12/1927 | Stenz | 434/263 |
| 1,659,315 | 2/1928 | Dailey | 206/63.5 |
| 1,709,066 | 4/1929 | Field | 434/263 |
| 3,346,957 | 10/1967 | Maurer et al. | 433/101 |
| 4,976,616 | 12/1990 | Eisner et al. | 433/77 |
| 5,244,394 | 9/1993 | Serabian-Musto | 434/263 |
| 5,348,154 | 9/1994 | Jacobs et al. | 206/369 |
| 5,356,294 | 10/1994 | Odomo | 433/229 |

FOREIGN PATENT DOCUMENTS 1290526  9/1972  United Kingdom .

*Primary Examiner*—John J. Wilson
*Attorney, Agent, or Firm*—Stephen R. Greiner

[57] ABSTRACT

A dental tray liner including a sheet configured to cover the bottom of a conventional dental tray. On the upper surface of the sheet is imprinted a chart of the teeth found in the human mouth with representations of the upper teeth arranged in a row adjacent similar representations of the lower teeth. During a dental examination, a user may easily note applicable dental conditions on the chart with a writing implement. After the examination, the user may, without touching the patient or liner, transcribe the information noted on the chart into a patient's permanent record without danger of spreading germs.

9 Claims, 4 Drawing Sheets

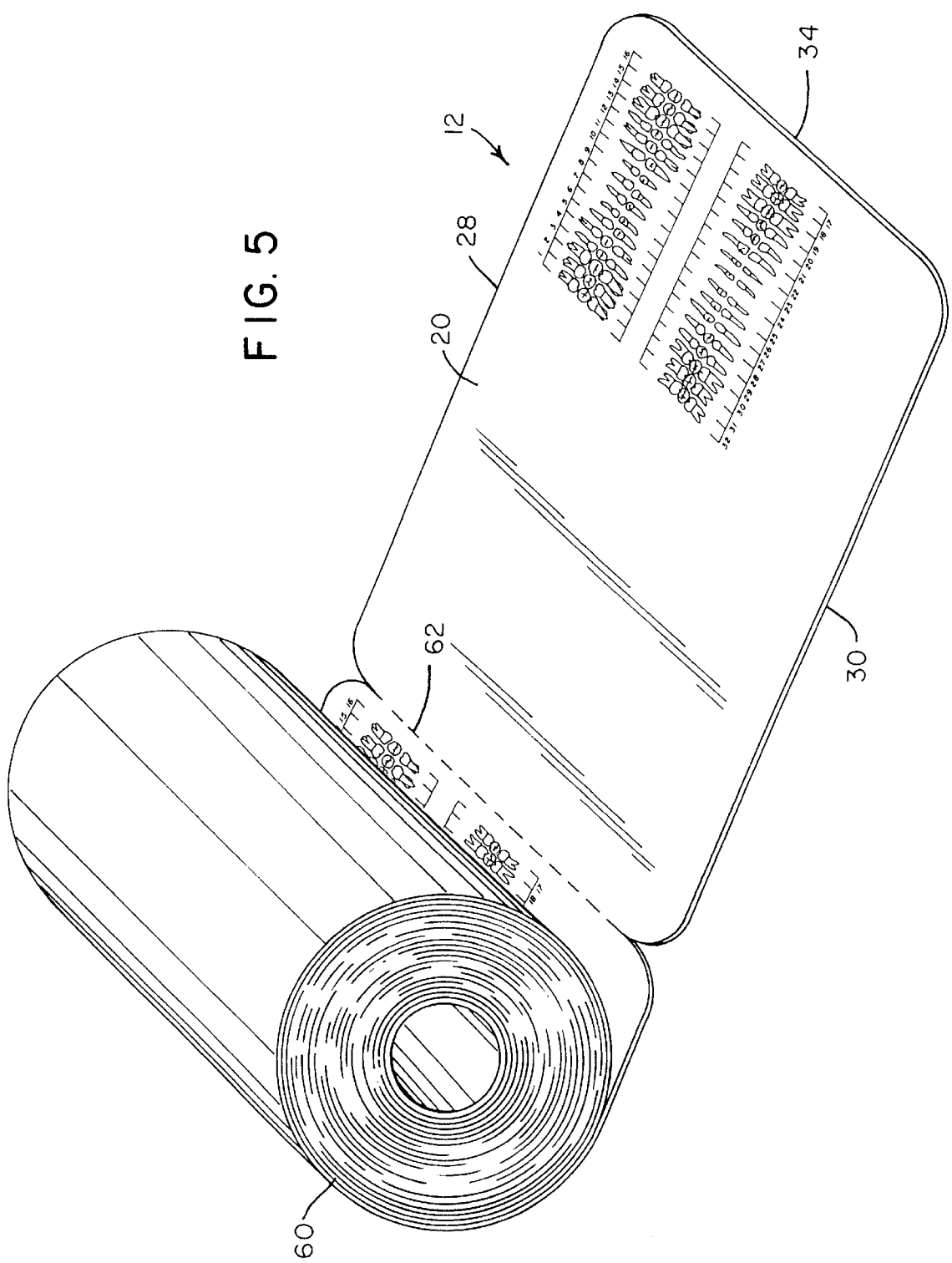

5,823,773

DENTAL TRAY LINER AND METHOD

FIELD OF THE INVENTION

The present invention relates generally to dentistry and, in particular, to a protective liner for use with a dental instrument tray.

BACKGROUND OF THE INVENTION

It is now standard practice for an individual seeking dental care to first meet with a hygienist upon entering a dentist's office. The hygienist will typically conduct an interview of the individual to establish a mutual trust and obtain a health history. Next, the hygienist will perform an examination of the teeth, oral cavity and associated structures of the individual.

The results of this examination are entered into a chart which becomes part of the individual's permanent record. The completed chart generally exhibits the locations of carious, broken and missing teeth. Any work previously performed by a dentist, including restorations, crowns and bridges, is also displayed. Because this information is used for treatment planning, evaluation, legal protection and patient identification, it must be complete and accurate.

The manual documentation of the dental conditions observed during an examination performed by a lone hygienist presents a significant challenge in preventing cross-contamination. The American Dental Association and other professional organizations have urged all dental professionals to avoid touching a patient's chart with hands which have been in contact with blood or saliva. Thus, combination dental probes and pens have been developed for temporarily noting examination results on the conventional, blank paper liners used on the dentist's bracket table or tray. These ad hoc notes are later transcribed from the contaminated liner when the hygienist has removed her gloves (or donned overgloves) to avoid contamination of the patient's permanent records.

Because an accurate account of an patient's dental health is so important, any transcription errors between the hygienist's jottings on the tray liner and the patient's permanent records cannot be tolerated. Unfortunately, determining the meaning of the original notes may be difficult once the examination of the patient has concluded. A need, therefore, exists for an improved dental tray liner which will assist a hygienist in rapidly documenting the condition of a patient's teeth, oral cavity and associated structures in a complete and accurate manner.

SUMMARY OF THE INVENTION

In light of the inadequacies of the prior art, it is a principal object of the invention to provide a dental tray liner with a chart of the teeth in the human mouth which may be easily marked with a writing implement to illustrate maladies within an individual's oral cavity and, from which, an account of these maladies may be transcribed into the individual's permanent records without spreading infectious germs to the individual's permanent records or elsewhere.

It is another object of the invention to provide a dental tray liner upon which a hygienist can clearly identify the location of carious teeth and the like and convey these findings to a dentist prior to his examination of the oral cavity without inducing needless anxiety in the patient by verbally describing these findings in the presence of the patient.

Still another object of the invention is to provide a dental tray liner upon which may be easily recorded essential facts accumulated from previous office visits prior to an examination. Thus, during the dental examination, the tray liner serves as a handy reminder to a dental professional that certain conditions, such as incipient caries, require monitoring.

It is a further object of the invention to provide a dental tray liner that can serve, at the discretion of a dental professional, as a visual aid to assist the patient in understanding where treatment is required within his oral cavity.

It is another object of the invention to provide a dental tray liner that is fabricated from inexpensive sheet materials such as paper or cardboard. A wax layer on the back side of the sheet prevents liquids from permeating through the paper or cardboard sheet and reduces the need to wash the dental tray. Of course, after a single use, the tray liner may be conveniently discarded.

It is an additional object of the invention to provide a plurality of dental tray liners of the type described in the form of a roll for easy distribution and dispensing.

It is an object of the invention to provide improved elements and arrangements thereof in a dental tray liner for the purposes described which is lightweight in manufacture, dependable and fully effective in accomplishing its intended purposes.

Briefly, the preferred tray liner constructed in accordance with this invention achieves the intended objects by featuring a sheet of liquid absorbent material. The sheet is about nine inches in width, and about thirteen and one-half inches in length. Printed indicia, forming a chart of the teeth of the human mouth, are located on the front side of the sheet so that dental maladies can be marked thereon with a writing implement. The lateral extent of the chart is preferably limited to less than one-half of that of the sheet so that dental tools placed on the sheet do not interfere with access to the chart. A flexible, wax coating is provided on the back side of the sheet to prevent liquid from permeating through the liner.

The foregoing and other objects, features and advantages of the present invention will become readily apparent upon further review of the following detailed description of the preferred embodiments as illustrated in the accompanying drawings.

BRIEF DESCRIPTION OF THE DRAWINGS

The present invention may be more readily described with reference to the accompanying drawings, in which:

FIG. 5 is a perspective view of a plurality of the preferred dental tray liners secured together for distribution in the form of a roll.

Similar reference characters denote corresponding features consistently throughout the accompanying drawings.

DETAILED DESCRIPTION OF THE PREFERRED EMBODIMENTS

Figure 1:
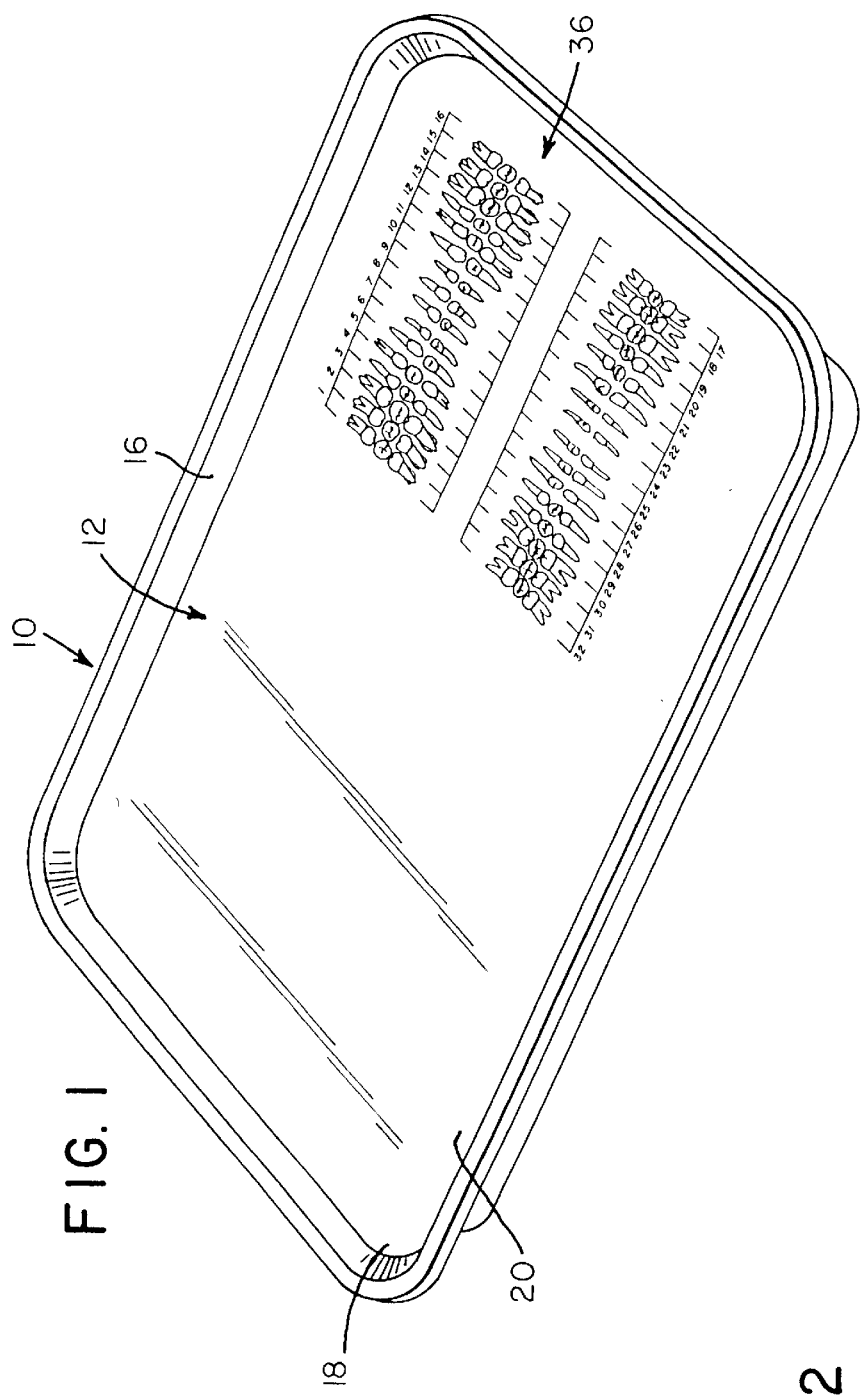
FIG. 1 is a perspective view of the preferred embodiment of a dental tray liner shown positioned on a dental tray.
Figure 2:
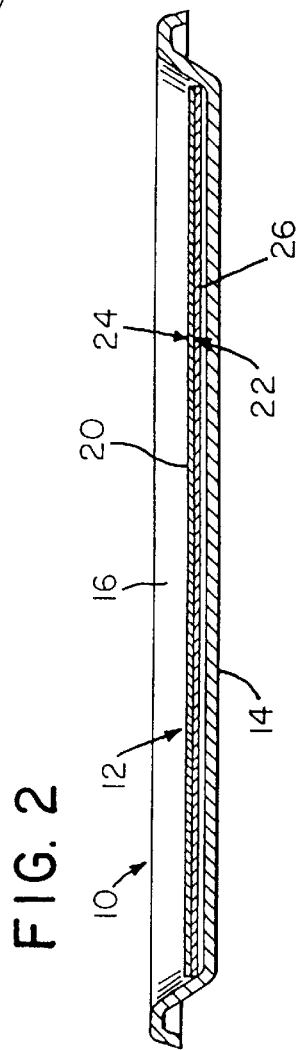
FIG. 2 is a lateral cross-sectional view of the preferred dental tray liner.
Figure 3:
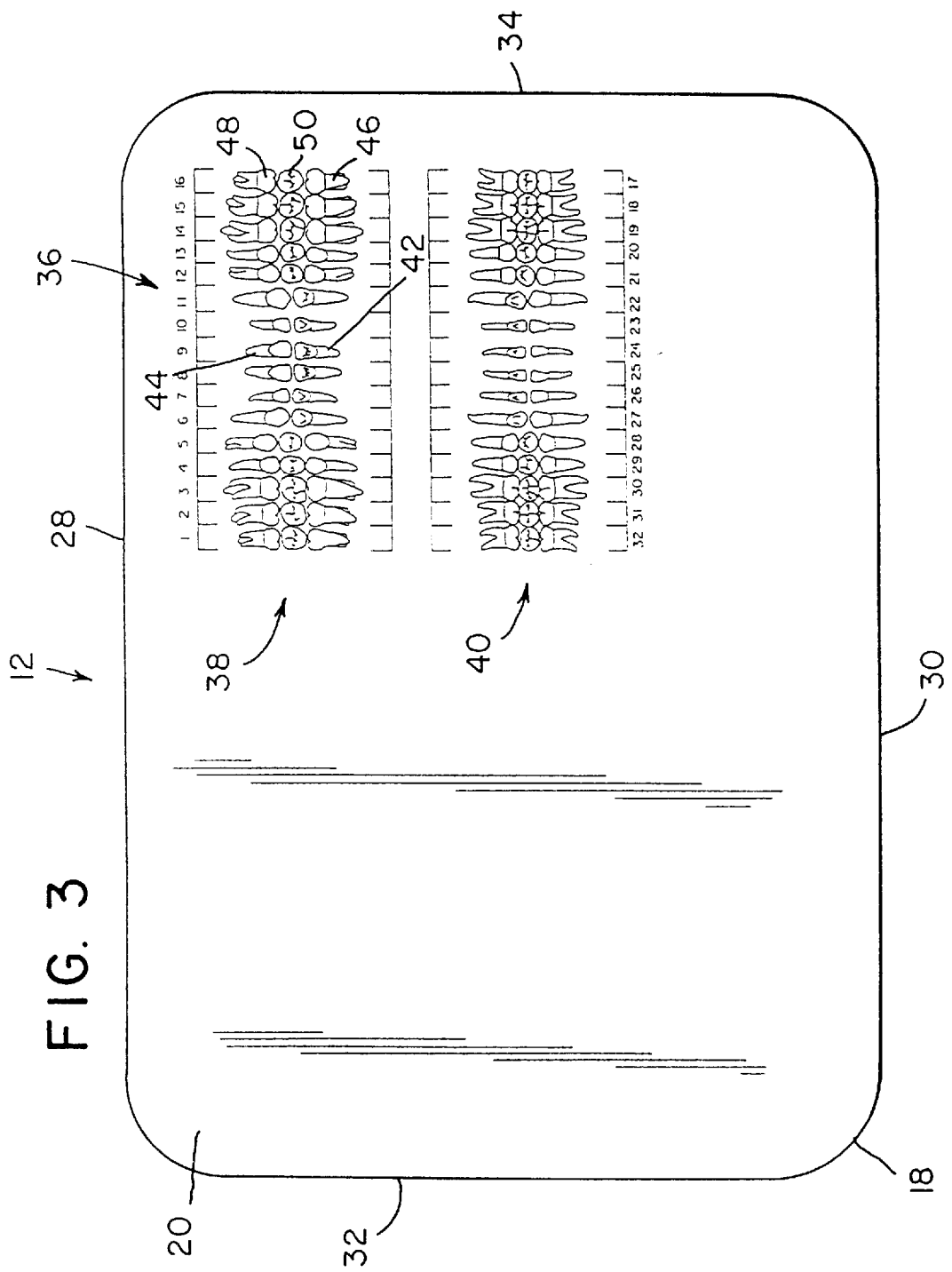
FIG. 3 is a top plan view of the preferred dental tray liner.

Referring now to FIGS. 1 through 3, a dental tray 10 is shown carrying a liner 12 constructed in accordance with the present invention. The tray 10 is provided with a generally rectangular bottom portion 14 which is bounded along its periphery by an upwardly-extending side wall 16. Preferably, the bottom portion 14 and side wall 16 are integrally formed from metal or plastic.

Positioned adjacent the bottom portion 14 of the tray 10 is the liner 12. The liner 12 serves to protect the bottom portion 14 and diminish the need for washing the tray 10. Preferably, the liner 12 is configured to closely conform to the rectangular outline of the bottom portion 14 of the tray 10 and, to this end, is provided with rounded corners as at 18.

The liner 12 preferably includes a sheet 20, having a back side 22 and a front side 24, formed from flexible paper stock. To prevent liquids from permeating through the liner 12 during use, the back side 22 of the sheet 20 is coated with a thin, wax layer 26. If desired, however, the sheet 20 may be formed from other suitable materials, such as cardboard, plastic or rubber, which are relatively inexpensive and capable of receiving wet dental instruments without substantially deteriorating.

The front side 24 of the sheet 20 preferably has a surface finish selected to promote ease of writing and to retain printed indicia of all types including the markings provided by ink pens, grease pencils and other suitable writing implements. The front side 24 of the sheet 20 is preferably not coated like the back side 22 thereof so that liquids, such as saliva or blood, may be absorbed by the sheet 20 itself.

The front side 24 of the sheet 20 has a top edge 28, a bottom edge 30, and a pair of opposed, left and right side edges 32 and 34 respectively. The sheet 20 measures approximately 9 inches (23 cm) in width from the top edge 28 of the sheet to the bottom edge 30 thereof. The sheet 20 is also approximately 13½ inches (34 cm) in length between the opposed side edges 32 and 34.

The sheet 20 is provided with printed indicia on its front side 24. Preferably, the indicia comprise a chart 36 displaying anatomic drawings of the teeth of an adult human. For easy reference, the upper teeth are numbered 1–16 in the chart 36 and are presented in side-by-side fashion in a single array 38. The lower teeth, on the other hand, are numbered 17–32 in the chart 36 and are likewise presented in an adjacent array 40.

Each tooth in the chart 36 is depicted by at least a pair of drawings corresponding to the shape of its inner surface and outer surface. The crown of each molar and premolar is also illustrated. For example, the tooth bearing the number "9" in the chart 36 is an incisor and is shown to have an inner surface 42 and an outer surface 44. The tooth bearing the number "16", however, is a molar and is shown to have an inner surface 46, an outer surface 48 and a crown 50.

So that access to the chart 36 is not unduly limited by the placement of tools and other dental implements on the sheet 20, the chart is positioned away from the center of the sheet itself. To accommodate right-handed users, the chart 36 is preferably located in the upper right-hand corner of the sheet 20 closely adjacent the edges 28 and 34 as shown. Also, by limiting the lateral extent of the chart 36 to less than one-half of that of the sheet 20 as shown, ample room is provided adjacent the chart for positioning probes, sharp explorers, mouth mirrors, dental floss, gauze sponges and other materials used during routine dental examinations.

Figure 4:
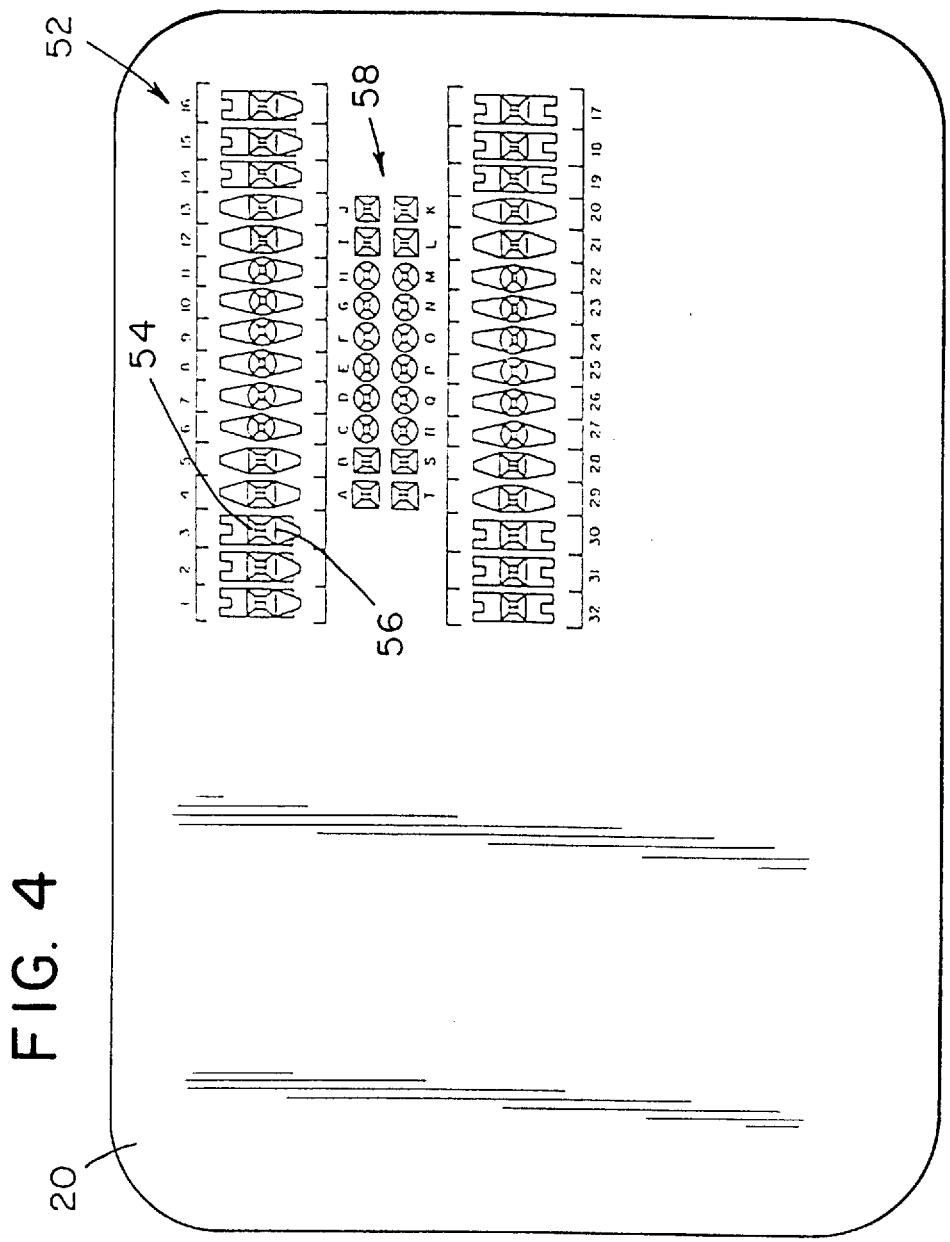
FIG. 4 is a top plan view of an alternative embodiment of a dental tray liner.

It is, of course, possible to vary form of the chart provided on the sheet 20. As shown in FIG. 4, for example, the chart 52 may alternatively include a diagrammatic representation of each tooth with a space for each exposed surface. Here, each tooth, like the one shown at position "3", is represented by two concentric and closed geometric shapes such as squares 54 and 56. The inner square 54 represents the occlusal surface of tooth "3" and may be divided into two portions. The outer square 56, which has been segmented into four parts, represents the mesial, facial, distal and lingual surfaces of the tooth "3".

The individual tooth diagrams are preferably arranged in a linear format but, may also be arranged in an arched form to simulate positioning within the oral cavity. Further, the chart 52 may include a series of diagrammatic representations illustrating the teeth in the mouth of a child as at 58. Rather than sequentially numbering the representations of the child's teeth, such may be designated by letters of the alphabet.

A hygienist will typically use a set pattern in accomplishing a complete and accurate charting of a patient's teeth with the liner 12. Typically, the hygienist will chart all of one type of condition for the entire mouth rather than completely chart each tooth. Such a procedure has been found to increase the speed and accuracy of the examination by focusing the hygienist's attention. For example, the hygienist will mark, with a suitable writing implement, the location of all restorations in their corresponding locations on the chart 36 or 52. Then, the hygienist will start again at the first tooth and record all deviations from normal such as the presence of caries and missing, unerupted or impacted teeth.

If sheet 12 is formed from impermeable plastic or rubber, then a grease pencil or crayon may be used to mark upon the chart 36. Grease pencils and crayons permit mistakes made by the hygienist in recording the conditions on the chart to be readily erased by rubbing them, for example, with a paper towel.

FIG. 5 illustrates that the dental tray liners in accordance with this invention may be produced and distributed in the form of a roll 60 with perforations 62 separating individual liners from one another. With the construction described, it should be apparent that the liners 12 may be dispensed from the roll 60 on an "as needed" basis simply by tearing along the perforations 62. If desired, the roll 60 may be suspended from a well-known hanger (not shown) for easy access.

Use of the novel liner, in any of its forms, will enable hygienists and other dental personnel to perform patient assessment activities with increased accuracy, efficiency and, most importantly, without spreading germs to the patient's permanent records or elsewhere. While the liner has been described with a high degree of particularity, it will be appreciated by those skilled in the art that numerous modifications and substitutions may be made thereto. Therefore, it is to be understood that the present invention is not limited to the embodiments described above, but encompasses any and all embodiments within the scope of the following claims.

I claim:

1. A dental tray liner, consisting of a sheet of paper having a front side and a back side, said front side having a chart of the teeth of a human mouth provided thereto, and said chart having a surface area that is substantially one-quarter of that of said sheet of paper.

2. The dental tray liner according to claim 1 wherein said chart is located substantially in one corner quadrant of said sheet of paper.

3. A dental tray liner, comprising:

a sheet of permeable material having a front side and a back side, said sheet having a top edge, a bottom edge, a right side edge and a left side edge; and, indicia located on said front side of said sheet, said indicia including geometric forms representing the teeth of the human mouth, said indicia having a lateral extent which is less than one-half of that of said sheet, and said indicia is positioned adjacent said top edge and said right side edge of said front side.

4. The dental tray liner according to claim 3 wherein said sheet is constructed of a material selected from a group consisting of paper, cardboard and plastic.

5. The dental tray liner according to claim 4 wherein the back side of said sheet is coated with an impermeable material.

6. The dental tray liner according to claim 3 wherein said sheet is approximately nine inches in width from said top edge of said sheet to said bottom edge of said sheet, and approximately thirteen and one-half inches in length between said right side edge of said sheet and said left side edge of said sheet.

7. The dental tray liner according to claim 3 wherein said indicia comprise anatomic drawings of human teeth positioned in a side-by-side relationship.

8. A dental tray liner assembly, comprising:

a roll of liquid absorbent material divided by perforations into a plurality of discrete sheets, each sheet having a front side and a back side, said front side of said sheet having a top edge, a bottom edge, a right side edge and a left side edge, said sheets being about nine inches in width from said top edge of each said sheet to said bottom edge thereof, and about thirteen and one-half inches in length between said right side edge of each said sheet and said left side edge thereof;

printed indicia located on said front side of each said sheet, said indicia including anatomic illustrations of the upper and lower teeth found in the human mouth, said indicia also having a lateral extent which is less than one-half of that of said sheet; and, a flexible, wax coating on the back side of each said sheet.

9. A method for recording dental conditions found during a manual examination of an individual positioned adjacent a tray holding dental and writing instruments, comprising the steps of:

positioning a sheet of material displaying representations of teeth within said tray;

placing upon said sheet a plurality of dental and writing instruments adjacent said representations of teeth;

probing the oral cavity of the individual with a dental instrument lifted from said sheet; and, marking, with a writing instrument lifted from said sheet, said representations of teeth displayed on said sheet so as to record the dental conditions observed in the oral cavity of the individual.

* * * * *